United States Patent
Foschini et al.

(10) Patent No.: US 12,033,761 B2
(45) Date of Patent: Jul. 9, 2024

(54) SENSOR-BASED MACHINE LEARNING IN A HEALTH PREDICTION ENVIRONMENT

(71) Applicant: Evidation Health, Inc., San Mateo, CA (US)

(72) Inventors: Luca Foschini, Santa Barbara, CA (US); Eamon Caddigan, Philadelphia, PA (US); Raghunandan Melkote Kainkaryam, Cincinnati, OH (US)

(73) Assignee: EVIDATION HEALTH, INC., San Mateo, CA (US)

(\*) Notice: Subject to any disclaimer, the term of this patent is extended or adjusted under 35 U.S.C. 154(b) by 111 days.

(21) Appl. No.: 16/926,510

(22) Filed: Jul. 10, 2020

(65) Prior Publication Data

US 2021/0241923 A1 Aug. 5, 2021

Related U.S. Application Data

(60) Provisional application No. 63/032,450, filed on May 29, 2020, provisional application No. 63/002,257, (Continued)

(51) Int. Cl.
*G16H 50/80* (2018.01)
*G06N 20/00* (2019.01)
(Continued)

(52) U.S. Cl.
CPC ............ *G16H 50/80* (2018.01); *G06N 20/00* (2019.01); *G16H 40/67* (2018.01); *G16H 50/20* (2018.01); *G16H 50/30* (2018.01); *G16H 50/70* (2018.01)

(58) Field of Classification Search
CPC ............ A61M 1/1611; A61M 1/1605; A61M 1/1613; A61M 1/1656; A61M 1/341;
(Continued)

(56) References Cited

U.S. PATENT DOCUMENTS 7,937,461 B2  5/2011  Kutzik et al.
10,327,697 B1  6/2019  Stein et al.
(Continued)

FOREIGN PATENT DOCUMENTS

IN  202041010784  11/2020
WO  WO-2014039881 A1  3/2014
(Continued)

OTHER PUBLICATIONS

E. Shillan, Duncan, et al. "Use of Machine Learning to Analyse Routinely Collected Intensive Care Unit Data: A Systematic Review." Critical Care 23 (2019) (Year: 2019).*
(Continued)

*Primary Examiner* — Amber A Misiaszek
(74) *Attorney, Agent, or Firm* — Wilson Sonsini Goodrich & Rosati

(57) ABSTRACT

A machine learning prediction system can analyze a dataset of users with self-reported symptoms and associated data from a wearable device to impact measure the impact of an acute health condition (such as the flu) at the population level. The machine learning prediction system can train a machine learning model to recognize individual acute health condition patterns based on differences in user activity with respect to the characteristics of determined baseline periods. For example, per-individual normalized change with respect to baseline aggregated at the population level can be used to determine individual acute health condition patterns and predict the onset of certain acute health conditions using a trained machine learning model. In response to predictions, the machine learning prediction system can take interventions to manage the impact of a predicted acute health condition on an individual.

21 Claims, 6 Drawing Sheets

Related U.S. Application Data filed on Mar. 30, 2020, provisional application No. 63/001,199, filed on Mar. 27, 2020, provisional application No. 62/968,086, filed on Jan. 30, 2020.

(51) Int. Cl.
*G16H 40/67* (2018.01)
*G16H 50/20* (2018.01)
*G16H 50/30* (2018.01)
*G16H 50/70* (2018.01)

(58) Field of Classification Search
CPC ..... A61M 1/1601; A61M 1/1654; G05B 6/02; G16H 20/40; G16H 40/40; G16H 40/63; G16H 50/20; G16H 50/30; G16H 50/50

See application file for complete search history.

(56) References Cited

U.S. PATENT DOCUMENTS

| | | | |
|---|---|---|---|
| 10,524,697 | B2 | 1/2020 | Gubbi Lakshminarasimha et al. |
| 11,056,242 | B1* | 7/2021 | Jain ................. G16H 10/60 |
| 11,127,506 | B1 | 9/2021 | Jain et al. |
| 11,387,000 | B2 | 7/2022 | Saliman et al. |
| 11,468,992 | B2 | 10/2022 | Pulicharam et al. |
| 11,471,115 | B2 | 10/2022 | Rance et al. |
| 2005/0228691 | A1 | 10/2005 | Paparo |
| 2006/0084847 | A1 | 4/2006 | Reed et al. |
| 2008/0146334 | A1 | 6/2008 | Kil |
| 2008/0214903 | A1 | 9/2008 | Orbach |
| 2008/0319786 | A1 | 12/2008 | Stivoric et al. |
| 2009/0006457 | A1 | 1/2009 | Stivoric et al. |
| 2011/0184250 | A1 | 7/2011 | Schmidt et al. |
| 2012/0046966 | A1 | 2/2012 | Chang et al. |
| 2012/0246102 | A1 | 9/2012 | Sudharsan |
| 2013/0004473 | A1 | 1/2013 | Kochel et al. |
| 2014/0005502 | A1 | 1/2014 | Klap et al. |
| 2014/0095417 | A1 | 4/2014 | Herz et al. |
| 2014/0129247 | A1* | 5/2014 | Op Den Buijs ....... G06Q 40/08 705/2 |
| 2014/0188512 | A1 | 7/2014 | Parker et al. |
| 2014/0278449 | A1 | 9/2014 | Kharraz Tavakol |
| 2014/0315168 | A1 | 10/2014 | Movellan et al. |
| 2015/0006456 | A1 | 1/2015 | Sudharsan |
| 2015/0242518 | A1 | 8/2015 | Rosenbaum et al. |
| 2016/0089089 | A1 | 3/2016 | Kakkar et al. |
| 2016/0142894 | A1* | 5/2016 | Papakonstantinou .. G16H 40/67 455/404.1 |
| 2016/0283686 | A1 | 9/2016 | Hu et al. |
| 2016/0328991 | A1 | 11/2016 | Simpson et al. |
| 2016/0361020 | A1 | 12/2016 | LeBoeuf et al. |
| 2017/0053091 | A1 | 2/2017 | Holmes et al. |
| 2017/0140109 | A1 | 5/2017 | Kheifetz et al. |
| 2017/0188841 | A1 | 7/2017 | Ma et al. |
| 2017/0206795 | A1* | 7/2017 | Kaleal, III ............. G16H 40/63 |
| 2017/0245808 | A1 | 8/2017 | Jain et al. |
| 2017/0249434 | A1 | 8/2017 | Brunner |
| 2017/0293846 | A1 | 10/2017 | Zyglowicz et al. |
| 2018/0338733 | A1 | 11/2018 | Jain et al. |
| 2018/0344215 | A1 | 12/2018 | Ohnemus et al. |
| 2018/0350451 | A1 | 12/2018 | Ohnemus et al. |
| 2019/0019581 | A1 | 1/2019 | Vaughan et al. |
| 2019/0043337 | A1* | 2/2019 | Liu ................. G16H 40/20 |
| 2019/0076031 | A1* | 3/2019 | Valys ................. A61B 5/02405 |
| 2019/0209022 | A1* | 7/2019 | Sobol ................. A61B 5/0022 |
| 2019/0245824 | A1 | 8/2019 | Hiir et al. |
| 2019/0287660 | A1 | 9/2019 | Oliveira et al. |
| 2019/0339291 | A1 | 11/2019 | Edmonds et al. |
| 2019/0355472 | A1 | 11/2019 | Kutzko |
| 2019/0385711 | A1 | 12/2019 | Shriberg et al. |
| 2020/0161005 | A1 | 5/2020 | Lyman et al. |
| 2020/0273578 | A1* | 8/2020 | Kutzko ................. G06N 20/00 |
| 2020/0302775 | A1* | 9/2020 | Liu ................. G06K 7/10366 |
| 2020/0372369 | A1 | 11/2020 | Gong et al. |
| 2021/0011443 | A1* | 1/2021 | McNamara ........... F24F 11/0001 |
| 2021/0038163 | A1 | 2/2021 | Agrawal et al. |
| 2021/0042667 | A1 | 2/2021 | Ghosh et al. |
| 2021/0113099 | A1 | 4/2021 | Rogers et al. |
| 2021/0117417 | A1 | 4/2021 | Hendrickson et al. |
| 2021/0151194 | A1 | 5/2021 | Foschini et al. |
| 2021/0151198 | A1 | 5/2021 | Sabeti et al. |
| 2021/0158214 | A1 | 5/2021 | Witt et al. |
| 2021/0166803 | A1 | 6/2021 | Ellis et al. |
| 2021/0174919 | A1 | 6/2021 | Vaughan |
| 2021/0182708 | A1 | 6/2021 | Park et al. |
| 2021/0201129 | A1 | 7/2021 | Schmude et al. |
| 2021/0319887 | A1 | 10/2021 | Derrick, Jr. et al. |
| 2022/0343160 | A1 | 10/2022 | Park et al. |
| 2023/0033835 | A1 | 2/2023 | Rathore et al. |
| 2023/0090138 | A1 | 3/2023 | Clay et al. |

FOREIGN PATENT DOCUMENTS

| | | |
|---|---|---|
| WO | WO 2019/165004 A1 | 8/2019 |
| WO | WO-2021127566 A1 | 6/2021 |
| WO | WO-2021154401 A1 | 8/2021 |
| WO | WO-2021222601 A1 | 11/2021 |
| WO | WO-2022200985 A1 | 9/2022 |
| WO | WO-2023044052 A1 | 3/2023 |
| WO | WO-2023114779 A1 | 6/2023 |

OTHER PUBLICATIONS

Althouse, B. M. et al., "Enhancing disease surveillance with novel data streams: challenges and opportunities," EPJ Data Science, vol. 4, Oct. 16, 2015, pp. 1-8.

Evidation Health, "Achievement," Date Unknown, six pages, [Online] [Retrieved on Nov. 4, 2020] Retrieved from the Internet <URL: https://www.myachievement.com/>.

Henning, K. J., "What is Syndromic Surveillance?," Morbidity and Mortality Weekly Report. Sep. 24, 2004, vol. 53, pp. 7-11.

Li, X. et al., "Digital Health: Tracking Physiomes and Activity Using Wearable Biosensors Reveals Useful Health-Related Information," PLoS Biology, Jan. 12, 2017, pp. 1-30.

Radin, J. M. et al., "Harnessing wearable device data to improve state-level real-time surveillance of influenza-like illness in the USA: a population-based study," The Lancet Digital Health, vol. 2, Iss. 2, Jan. 16, 2020, pp. e85-e93.

Simonsen, L. et al., "Infectious Disease Surveillance in the Big Data Era: Towards Faster and Locally Relevant Systems," The Journal of Infectious Diseases, vol. 214, Issue suppl. 4, Dec. 2016, pp. S380-S385.

U.S. Food & Drug Administration, "Real-World Evidence," Mar. 23, 2020, three pages, [Online] [Retrieved on Nov. 4, 2020] Retrieved from the Internet <URL: https://www.fda.gov/science-research/science-and-research-special-topics/real-world-evidence>.

PCT International Search Report and Written Opinion, PCT Application No. PCT/US2020/064369, Mar. 2, 2021, 23 pages.

Homayounfar et al.: Data mining research trends in computerized patient records. 2011 Federated Conference on Computer Science and Information Systems (FedCSIS), pp. 133-139 (2011).

Pavel et al.: Behavioral Informatics and Computational Modeling in Support of Proactive Health Management and Care. IEEE Transactions on Biomedical Engineering. 62(12):2763-2775 doi:10.1109/TBME.2015.2484286 (2015).

Pentland: Healthwear: medical technology becomes wearable. Computer 37(5), pp. 42-49 doi:10.1109/MC.2004.1297238 (2004).

U.S. Appl. No. 16/953,256 Non-Final Office Action dated Jan. 5, 2023.

U.S. Appl. No. 17/968,413 Non-Final Office Action dated Jan. 3, 2023.

Co-pending U.S. Appl. No. 17/111,765, inventors Foschini; Luca et al., filed Dec. 4, 2020.

Co-pending U.S. Appl. No. 17/968,413, inventors Foschini; Luca et al., filed Oct. 18, 2022.

U.S. Appl. No. 17/946,975 Non-Final Office Acton dated Nov. 17, 2022.

PCT/US2022/043874 International Search Report and Written Opinion dated Nov. 17, 2022.

(56) References Cited

OTHER PUBLICATIONS

U.S. Appl. No. 17/946,975 Final Office Action dated May 5, 2023.
PCT/US2022/081465 International Search Report and Written Opinion dated May 9, 2023.
U.S. Appl. No. 17/968,413 Final Office Action dated Jun. 7, 2023.
Co-pending U.S. Appl. No. 18/148,991, inventors Foschini; Luca et al., filed Dec. 30, 2022.
Co-pending U.S. Appl. No. 18/156,010, inventors Foschini; Luca et al., filed Jan. 18, 2023.
Mezlini et al.: Estimating the Burden of Influenza-like Illness on Daily Activity at the Population Scale Using Commercial Wearable Sensors. JAMA Netw Open. 5(5):e2211958:1-12 doi:10.1001/jamanetworkopen.2022.11958 (2022).
PCT/US2022/081465 Invitation to Pay Additional Fees dated Mar. 2, 2023.
Qayyum et al.: Secure and Robust Machine Learning for Healthcare: A Survey. IEEE Reviews in Biomedical Engineering, vol. 14, pp. 156-188 doi:10.1109/RBME.2020.3013489 (2020).
U.S. Appl. No. 17/111,765 Non-Final Office Action dated Feb. 17, 2023.
U.S. Appl. No. 17/946,975 Non-Final Office Action restarting Office Action dated Nov. 17, 2022, mailed on Jan. 11, 2023.
U.S. Appl. No. 18/156,010 Non-Final Office Action dated Mar. 22, 2023.
Atito et al.: MC-SSL0.0: Towards Multi-Concept Self-Supervised Learning. arXiv:2111.15340, pp. 1-17 [pre-print] (2021).
Kolbeinsson et al.: Self-supervision of wearable sensors time-series data for influenza detection. arXiv:2112.13755, pp. 1-5 [pre-print] DOI:10.48550/arXiv.2112.13755 [retrieved online Jun. 20, 2023] (2021).
PCT/US2023/060815 International Search Report and Written Opinion dated Jun. 5, 2023.
Suo et al.: GLIMA: Global and Local Time Series Imputation with Multi-directional Attention Learning. 2020 IEEE International Conference on Big Data (Big Data), Atlanta, GA, USA, pp. 798-807. DOI:10.1109/BigData50022.2020.9378408 (2020).
Cao et al.: DeepMood: Modeling Mobile Phone Typing Dynamics for Mood Detection. arXiv:1803.08986, pp. 1-9 doi:10.1145/3097983.3098086 (2018).
Daly et al.: Risk stratification and daily symptom monitoring for oncology patients. Journal of Clinical Oncology 37(15)Suppl., p. 6535 DOI:10.1200/JCO.2019.37.15_suppl.6535 (2019).
Element AI: Element AI makes its BAyesian Active Learning library open source. (Retrieved online on Jan. 21, 2021), pp. 1-6 URL: https://www.elementai.cominews/2019/element-ai-makes-its-bayesian-active-learning-library-open-source (2019).
Gal et al.: Bayesian convolutional neural networks with Bernoulli approximate variational inference. ICLR workshop track arXiv:1506.02158, pp. 1-12 doi:10.48550/ARXIV.1506.02158 (2016).
Gal et al.: Deep Bayesian Active Learning with Image Data. arXiv:1703.02910, pp. 1-10 doi:10.48550/ARXIV.1703.02910 (2017).
Gal et al.: Dropout as a Bayesian approximation: Representing model uncertainty in deep learning. International Conference on Machine Learning, pp. 1-10 URL: http://proceedings.mlr.press/v48/gal16.pdf (2016).
Hochreiter et al. Long Short-Term Memory. Neural Computation 9(8):1735-1780 (1997).
Houlsby et al.: Bayesian Active Learning for Classification and Preference Learning. arXiv:1112.5745, pp. 1-17 doi:10.48550/ARXIV.1112.5745 (2011).
Nelson et al.: Continuous, objective measurement of physical activity during chemotherapy for breast cancer: the Activity in Treatment pilot study. Transl Behav Med. 10(4):1031-1038 doi:10.1093/tbm/ibz079 (2020).
Schroeder et al.: Examining Self-Tracking by People with Migraine: Goals, Needs, and Opportunities in a Chronic Health Condition. DIS 2018, pp. 135-148 DOI:10.1145/3196709.3196738 (2018).
Turner: New directions in communications (or Which way to the Information Age?). IEEE Communications Magazine 24(10):8-15 doi:10.1109/MCOM.1986.1092946 (1986).
U.S. Appl. No. 14/977,194 Final Office Action dated Dec. 16, 2016.
U.S. Appl. No. 14/977,194 Final Office Action dated Jul. 12, 2018.
U.S. Appl. No. 14/977,194 Final Office Action dated May 21, 2020.
U.S. Appl. No. 14/977,194 Non-Final Office Action dated Aug. 30, 2017.
U.S. Appl. No. 14/977,194 Non-Final Office Action dated Feb. 25, 2016.
U.S. Appl. No. 14/977,194 Non-Final Office Action dated Sep. 26, 2019.
Wang et al.: Unsupervised learning of disease progression models. KDD '14: Proceedings of the 20th ACM SIGKDD international conference on Knowledge discovery and data mining, pp. 85-94 URL:https://doi.org/10.1145/2623330.2623754 (Aug. 2014).

\* cited by examiner

SENSOR-BASED MACHINE LEARNING IN A HEALTH PREDICTION ENVIRONMENT

CROSS REFERENCE TO RELATED APPLICATIONS

This application incorporates by reference U.S. Provisional Application No. 62/968,086, filed Jan. 30, 2020, U.S. Provisional Application No. 63/001,199, filed Mar. 27, 2020, U.S. Provisional Application No. 63/002,257, filed Mar. 30, 2020, and U.S. Provisional Application No. 63/032,450, filed May 29, 2020.

BACKGROUND

This disclosure generally relates to managing and, in particular, to predicting or detecting the effects of an acute health condition based on physical statistic data.

Influenza-like illnesses and other acute health conditions (AHCs) can be unpredictable to the average person in both onset and recovery. For many AHCs, such as the flu, only a small percentage of events are reported to the health care system, leaving the majority of the burden of the acute health condition on society unassessed. Further, even when cases of the acute health condition are reported to the health care system, the burden in terms of lost productivity (sick days), sleep deprivation, and overall decrease in health status is unmeasured using traditional methods. Similarly, because many cases of acute health conditions are left unreported to the healthcare system, interventions or techniques to manage the impact of the acute health condition may not be adequately communicated an affected user.

SUMMARY

Sensor data about a user (for example, from wearable devices) can reflect physiological and behavioral changes associated with infectious disease contagion (for example, the onset of Lyme disease or influenza in a single individual) or other AHCs.

A machine learning prediction system can analyze a dataset of users with self-reported symptoms and associated data from a wearable device to measure the impact of an acute health condition (such as the flu) at the population level. For example, impact can be measured in terms of lost physical activity, increased sleep requirements, and changes in resting heart rate. Using the wearable data and acute health condition event data, the machine learning prediction system can estimate normal activity periods by learning from the dataset. For example, the machine learning prediction system can train a machine learning model on days the user is not affected by an acute health condition based on the wearable data of one or more users (or a sub-population of users) of the population.

Similarly, the machine learning prediction system can learn individual acute health condition patterns (and, in some embodiments, train a machine learning model to predict acute health condition impact) by analyzing differences in user activity with respect to the characteristics of the determined baseline periods. For example, a per-individual normalized change with respect to baseline (individual-level z-score) aggregated at the population level can be used to determine individual acute health condition patterns and predict the onset of certain acute health conditions. In response to predictions, the machine learning prediction system can take interventions to manage the impact of a predicted acute health condition on an individual (or on a group or population the individual is a member of).

Figure 1:
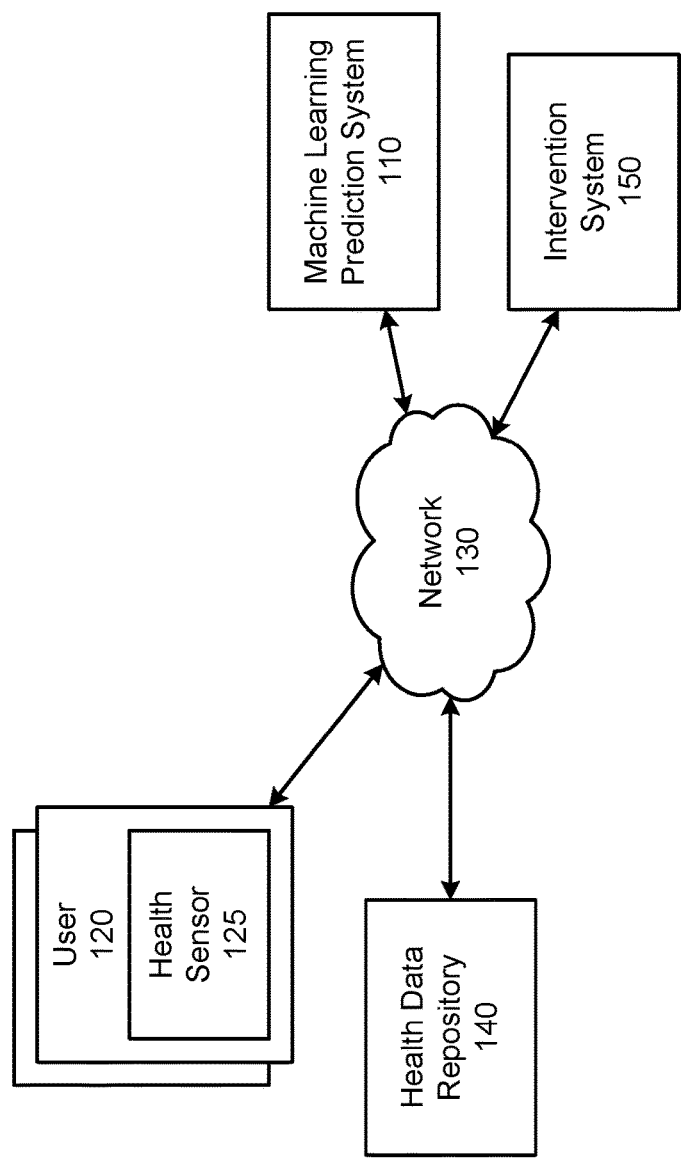
FIG. 1 is a block diagram of a system environment in which a machine learning prediction system operates, in accordance with an embodiment.

The figures depict various embodiments for purposes of illustration only. One skilled in the art will readily recognize from the following discussion that alternative embodiments of the structures and methods illustrated herein may be employed without departing from the principles described herein. The figures use like reference numerals to identify like elements. A letter after a reference numeral, such as "110A," indicates the text refers specifically to the element having that particular reference numeral. A reference numeral in the text without a following letter, such as "102," refers to any or all of the elements in the figures bearing that reference numeral (e.g., "110" in the text refers to reference numerals "110A" and "110B" in the figures).

DESCRIPTION

A machine learning prediction system can utilize sensor data reflecting physiological and behavioral changes associated with an acute health condition to predict the effects of the acute health condition on individual users or a population (or population cohort) of users. An acute health condition (AHC), as used herein, is an illness, injury, or other health state associated with physiological and behavioral changes relative to a measurable baseline health state. In some embodiments, acute health conditions have a measurable onset and a recovery period before an individual who recovers returns to a baseline health state. For example, an acute health condition can be the flu (influenza) or another ILI (Influenza-Like Illness) such as $H_1N_1$ or COVID-19, another disease or illness such as a cold or Lyme disease, an acute injury, or a post-medical procedure recovery period due to a procedure that has immediate reflection on behavior or physiological signals such as total knee arthroscopy or bariatric surgery. In some implementations, a machine learning prediction system can be used to predict the effects of an acute health condition with an impact on a short enough timescale that certain portions of an individual's history can be safely assumed to not be affected by the acute health condition. For example, the assumed unaffected portions (e.g., portions of the individual's history that are not affected by the acute health condition) can be used for training a baseline model with regard to the unaffected state of the individual. More challenges can exist when predicting the impact of chronic conditions, which can go undiagnosed for a long time and may affect activity in a latent way harder to distinguish from a baseline level for if the individual was not affected by the chronic condition.

For example, a machine learning prediction system can measure the burden of the flu on a population based on retrospective data about a population of users. By learning what flu patterns look like, the system can, for instance, quantify that an average of 10,000 steps/day are lost for people affected by the flu (as a population level average), or 30 minutes of additional sleep are needed during 2+ days during the flu period, or the average RHR (resting heart rate) increases by 1 beat/minute for 3 days on average when a user is affected by the flu.

Measuring the burden of the flu (or another AHC) within a population can provide public health benefits, because only a small percentage of flu events are reported to the health care system, leaving the majority of the burden of the flu on society unassessed. Further, even when cases of the flu are reported to the health care system, the burden in terms of lost productivity (sick days), sleep deprivation, and overall decrease in health status is unmeasured using traditional methods. Additionally, flu burden measurement via activity data can be accurate and fine grained, allowing for comparative effectiveness analyses of different flu treatments (e.g., antivirals) or vaccine impact in modulating the disease in real world settings.

Once the machine learning prediction system trains a machine learning model (or simply, "model" hereinafter) of flu impact (for example, decreasing steps over 3 days of more than 3%, increase of RHR from day 2, 10+ minutes sleep lost for more than 2 days), then the system can detect the flu's onset in individuals, and potentially offer an individualized prediction or prognosis (such as of the future impact of the flu on that individual). Then, after the system learns the patterns of flu at the individual level, the machine learning prediction system can aggregate patterns to look for those patterns occurrence in real time data and gauge the state of an epidemic for example, to forecast the impact of the flu based on current data. In some implementations, the machine learning prediction system 110 predicts the onset of the flu in an individual before it occurs using a machine learning model. For example, a model can be trained to predict the probability that a user will report the onset of flu 72-120 hours in the future using activity and other contextual data (such as weather, age, and geographical location) gathered from the preceding days. In some implementations, these predictions by the machine learning prediction system are used to generate one or more interventions to manage the impact of the predicted case of the AHC. For example, the prediction might be sent to an application running on a client device of the user and/or the health care provider, and information about the prediction can be displayed in a user interface (e.g., the probability that the user will report the flu and other analysis conducted related to that probability).

System Overview

FIG. 1 is a block diagram of a system environment in which a machine learning prediction system operates, in accordance with an embodiment. The environment 100 of FIG. 1 includes a machine learning prediction system 110, a set of users 120 associated with one or more health sensors 125, a network 130, a health data database 140, and an intervention system 150.

The machine learning prediction system 110 is a server, server cluster, or cloud-based server capable of predicting the onset or impact of one or more acute health conditions on a population or individual users within a population based on physical statistics received from users 120 in the population. In some embodiments, the machine learning prediction system 110 gathers physical statistics about a set of users 120 within a population (for example, through data from one or more health sensors monitoring the physical statistics of users 120) and uses the resulting data to predict acute health condition impacts. As used herein, physical statistics are measurements characterizing a user's activity level or current health state. For example, physical statistics can include measurements of the user's vital signs such as resting heart rate (RHR), current heart rate (for example, presented as a time series), heart rate variability, respiration rate, or galvanic skin response, measurements of user activity such as daily number of steps, distance walked, time active, or exercise amount, sleep statistics such as time slept, number of times sleep was interrupted, or sleep start and end times, and/or other similar metrics. The machine learning prediction system 110 can analyze the received physical statistic data to extrapolate population level statistics about one or more acute health conditions. Similarly, the machine learning prediction system can generate AHC impact models using physical statistic data to predict acute health condition onset (or monitor acute health condition recovery) among individual users 120 within the population. In some implementations, the machine learning prediction system 110 can perform or recommend interventions on a population, population cohort, group, or individual level based on the determined population level statistics and/or predictions based on AHC impact models. The machine learning prediction system 110 will be discussed further below.

Each user 120 of the machine learning prediction system 110 is a member of a population monitored by the machine learning prediction system 110 for one or more AHCs. A user 120 can interact with health sensors 125 and the machine learning prediction system 110 through a mobile device, laptop or desktop computer, or other similar computing device. In some implementations, each user 120 is a member of one or more population cohorts characterized by demographic information, geographic location, user characteristics and/or other similar factors. A user can additionally be a member of one or more groups representing users associated with the same place of employment, attendance of a planned event, a small geographic location, or the like.

In some embodiments, each user 120 is associated with a set of health sensors 125 measuring physical statistics of that user 120. For example, the set of health sensors 125 associated with a user 120 can measure physical statistics such as the user's resting heart rate (RHR) over time, daily number of steps (and/or other measures of activity level such as distance walked or time active), and sleep statistics (such as time slept, number of times sleep was interrupted, sleep start and end times, and the like) for the user 120. The recorded physical statistics can be stored and sent by the health sensor 125 as physical statistic data can then be sent to the machine learning prediction system 110 for analysis. In some implementations, some or all physical statistic data is collected in the form of time series data consistently recording measurements of physical statistics of the user over time. The frequency of measurements included in the physical statistics data sent to the machine learning prediction system 110 can depend on the health sensor 125, user preference selections, and the type of physical statistic data being collected. For example, a health sensor 125 may send time series data for average RHR multiple times per day, but only send hours slept data once per day. In some implementations, the health sensor 125 sends physical statistic data to the machine learning prediction system 110 frequently, for example daily or in real time.

A health sensor 125 can be a wearable device or other device capable of providing physical statistics about the user 120. For example, a health sensor 125 can be a dedicated fitness tracker, a pedometer, a sleep tracker, a smart watch, smartphone, or mobile device with physical statistic monitoring functionality. For example, a health sensor 125 can be a smartphone of the user 120 with an installed physical statistic monitoring application using one or more sensors of the smartphone to measure steps, activity, movement, sleep time, or other physical statistics. An individual user 120 can be associated with multiple health sensors 125 measuring overlapping or distinct physical statistics about the user 120. The physical statistic data gathered by health sensors 125 can be sent to the machine learning prediction system 110 directly from the health sensor 125, manually uploaded to the machine learning prediction system 110 by the associated user 120 or transmitted via a third-party system to the machine learning prediction system 110. For example, the user 120 may authorize a third-party service associated with a health sensor 125 to transmit physical activity data to the machine learning prediction system 110. A user 120 or a health sensor 125 associated with a user 120 can communicate with the machine learning prediction system 110 over the network 130.

The network 130 is a network or system of networks connecting the machine learning prediction system 110 to the set of users 120 and/or health sensors 125 associated with a user 120. The network 130 may comprise any combination of local area and/or wide area networks, using wired and/or wireless communication systems. In one embodiment, the network 130 uses standard communications technologies and/or protocols. For example, the network 130 can include communication links using technologies such as Ethernet, 3G, 4G, 5G, CDMA, WIFI, and Bluetooth. Data exchanged over the network 130 may be represented using any suitable format, such as hypertext markup language (HTML) or extensible markup language (XML). In some embodiments, all or some of the communication links of the network 130 may be encrypted using any suitable technique or techniques. In some implementations, the network 130 also facilitates communication between the machine learning prediction system 110, users 120, and other entities of the environment 100 such as the health data database 140, the intervention system 150, and/or the user group system 160.

The health data repository 140 stores acute condition information about one or more users 120. For example, the health data repository 140 can be a medical provider or other entity storing records of acute health conditions. For example, a health data repository 140 can store information regarding a surgical procedure a user 120 underwent. In some implementations, users 120 can send or have sent to the machine learning prediction system 110 information about one or more acute health conditions stored in the health data repository 140. The health data repository 140 can include a server, server cluster, or other computing system with a database or other data storage system.

The intervention system 150 is a server, set of servers, server cluster, or other computing system which can perform interventions recommended by the machine learning prediction system 110. As used herein, an "intervention" is an action initiated by the machine learning prediction system 110 to reduce, mitigate, or otherwise respond to the effects of a predicted AHC on an individual or population. In some implementations, one or more interventions are directly performed by the machine learning prediction system 110, such as providing a recommendation to the user 120, however, other interventions may require additional resources or authorization not available to the machine learning prediction system 110. Only one intervention system 150 is shown in FIG. 1 for clarity, but the machine learning prediction system 110 can interface with multiple intervention systems 150 to enable performance of different interventions.

As well be discussed further below, the interventions recommended by the machine learning prediction system 110 can depend on the AHC and the specific predictions made by the machine learning prediction system 110. For example, in some implementations a machine learning prediction system 110 can predict that an individual user 120 has an AHC and recommended the intervention of a diagnostic-level test to confirm that the user 120 has the AHC. In this case the machine learning prediction system 110 can partner with an intervention system 150 that is a test provider capable of performing and determining the results of a suitable test. Similarly, an intervention system 150 can be a medical provider of the user 120 which may schedule a follow up appointment or the like to confirm the predictions of the machine learning prediction system 110 and take appropriate actions. In some embodiments, an intervention system 150 can also take population or group-level action based on a recommended intervention by the machine learning prediction system 110 based on population-level statistics or aggregated individual predictions for a group. In these embodiments, the intervention system 150 can be a government entity (such as a city or county level government entity), or a group administrator (such as an employer or an event organizer).

Figure 2:
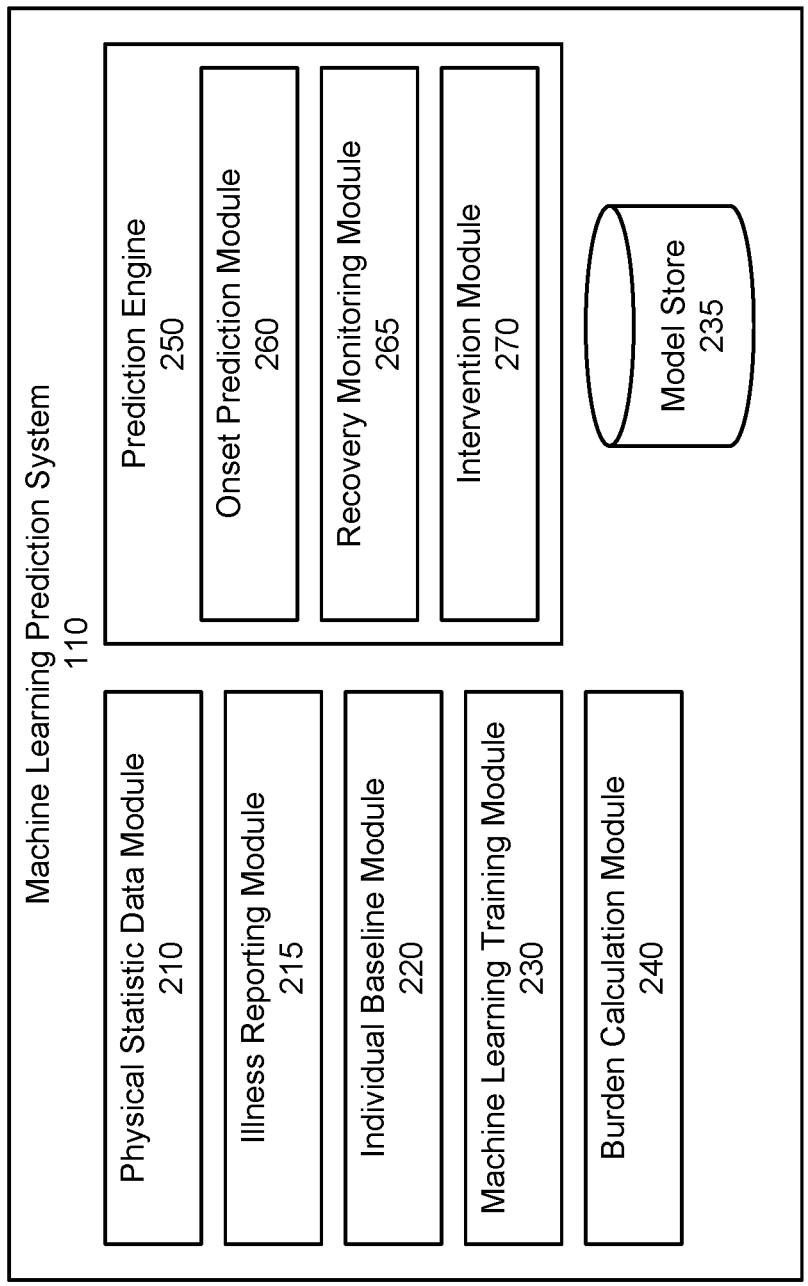
FIG. 2 is a block diagram of a machine learning prediction system, in accordance with an embodiment.

FIG. 2 is a block diagram of a machine learning prediction system, in accordance with an embodiment. FIG. 2 shows a machine learning prediction system 110 including a physical statistic data module 210, an illness reporting module 215, an individual baseline module 220, a model training module 230, a model store 235, a burden calculation engine 240, and a prediction engine 250. In other embodiments, the machine learning prediction system 110 may include additional, fewer, or different components for various applications. Conventional components such as network interfaces, security functions, load balancers, failover servers, management and network operations consoles, and the like are not shown so as to not obscure the details of the system architecture. In some embodiments, machine learning prediction system 110 can monitor a set of users 120 for multiple AHCs simultaneously, as described above. In some implementations, each module of the machine learning prediction system 110 can simultaneously perform its function for multiple distinct AHCs and, in some cases, gathered data (such as physical statistic data) can be applicable to the analysis for multiple AHCs affecting the same physical statistics.

Data Gathering

The physical statistic data module 210 of the machine learning prediction system 110 can monitor a set of physical statistics about the set of users 120. In some implementations, the physical statistic data module 210 gathers time series datasets representing measures of the set of physical statistics of a user over time ("physical statistic data"). The physical statistic data module 210 can receive physical statistic data, process it for use by the machine learning prediction system 110, and store the physical statistic data. As described above, the physical statistic data for a user can include readings from one or more health sensors 125 associated with the user, however the physical statistic data module 210 can collect physical statistic data from other sources, such as by being logged or otherwise manually input by the associated user 120, from a health data repository 140, or from another similar source.

The physical statistic data module 210 can preprocess received physical statistic data prior further analysis by the machine learning prediction system 110. The machine learning prediction system 110 receives physical statistic data from multiple different types or models of health sensors 125 (or other sources) which can report physical statistic data in different formats and using different conventions. For example, the frequency of data points in received time series data can differ between physical statistic data collected from different health sensors 125 (even if both measure the same statistics). In some implementations, the physical statistic data module 210 can standardize received physical statistic data for further analysis, such as by transforming received time series data to be consistent across the set of physical statistic data and/or computing secondary physical statistic data from received physical statistic data. For example, the physical statistic data module 210 can receive physical statistic data for a user 120 including a rolling 5 minute average of heart rate measurements and activity data for a user and preprocess the data to a daily RHR, step count, time spent active, and sleep time (for example, determined based on a combination of time, heart rate, and activity data) for the user 120 for each data was received.

Each physical statistic monitored by the machine learning prediction system 110 can be affected by one or more AHCs. In some embodiments, physical statistic data collected by the physical statistic data module 210 can be used both in training models (along with symptom data gathered by the symptom data module 215) and for predicting AHC impact based on the generated models in real time or in near-real time. In some implementations, the physical statistic data module 210 continuously receives physical statistic data from health sensors 125 or users and preprocesses the physical statistic data for evaluation in real time or near-real time (for example, for predicting the onset of an AHC).

The illness reporting module 215 can collect reports of users 120 who have had an AHC. Users 120 can self-report having an AHC to the machine learning prediction system 110 and on which days they were affected by the AHC. In some implementations, the illness reporting module 215 can receive information on users who have had an AHC from another authorized source, such as a health data repository (if requested by or consented to by the user 120). In some implementations, the illness reporting module 215 sends surveys to users 120 (for example via a mobile device of the user 120) to determine if they had an AHC (and, in the case of a machine learning prediction system 110 monitoring multiple AHCs, which AHC). In some implementations, the surveys directly ask if the user 120 had a specific AHC, but surveys sent by the illness reporting module 215 can also ask about a set of symptoms characteristic of the AHC which can indicate if a user had the AHC and on which days they were affected by the symptoms. For example, the illness reporting module 215 can query users 120 as to whether they had experienced flu-like (ILI) symptoms in the preceding 14 days. Responding users 120 who had experienced symptoms were then asked to identify symptom days. Those who had not experienced symptoms were queried again two weeks later. The illness reporting module 215 can infer that users who reported symptoms had an ILI on the reported symptom days.

After determining that a user 120 had an AHC, the illness reporting module 215 can cross-reference physical statistic data for that user for the time period around and during the reported AHC. The illness reporting module 215 can label physical statistic data collected for that user 120 for the time period with an AHC event or log a separate AHC event for the user 120 those days. This data can be later used by the AHC to estimate the burden of the AHC on the population and to model (or improve a current model of) the AHC for making predictions related to the AHC. In some implementations, a user 120 self-reporting an AHC in real time (or near-real time) can trigger the machine learning prediction system 110 to monitor the recovery of the user 120 from the AHC.

User Baseline Estimation

As described above, the machine learning prediction system 110 can determine what "normal" activity for a user 120 looks like in physical statistic data, by training a model on days the user isn't (or is presumed to not be) affected by an AHC. In some implementations, the machine learning prediction system 110 models what user physical statistic data (such as activity, sleep, and RHR) would look like for an individual user 120 over a certain period of time if the user 120 had not had an AHC in that time period. If the user 120 did report an AHC event for that period of time, this task equates to modeling the counterfactual situation in which that individual didn't have the AHC.

In some implementations, the individual baseline module 220 computes an average/standard deviation of user physical statistic data over a baseline period (during which the machine learning prediction system 110 infers the user 120 didn't report an AHC) and assume that during an AHC the user 120 would have exhibited the same physical statistic data patterns. In other implementations, the individual baseline module 220 can use one or more statistical models in which physical statistic data (such as steps, sleep, RHR) for individual user i at day j is modeled as a function of other users $i' \neq i$ similar to user i and other days $j' \neq j$. For example, embodiments can use time series models (such as ARIMA (p, d, q)) with covariates and time-varying variables such as day-of-week or cross-sectional models using individual user-specific variables (such as demographics) to learn from similar users 120.

The individual baseline module 220 can additionally use modern machine learning models to estimate non-AHC baselines for a user 120. An individual machine learning model can be trained to estimate the activity of individual user i at day j based on all information available from other user 120 and other days, including contextual information (such as weather). Forecasting techniques based on "deep learning" can outperform classical approaches when calculating individual user 120 baselines. In some implementations, a machine learning prediction system 110 uses a model embedding of the total amount of physical statistic data and contextual data in non-AHC periods e.g., via deep autoencoder. This approach can be used to model resting heart rate (RHR) using other physical statistics (such as steps and sleep state).

Acute Health Condition Modeling

The machine learning training module 230 generates AHC impact models that can be used by the machine learning prediction system 110 to estimate the burden of the associated AHC on a population or to predict the onset of the AHC in an individual, according to some embodiments. The generated AHC impact models can be stored in a database or other data storage system of the model store 235 for retrieval and use by other parts of the machine learning prediction system 110.

An AHC impact model can predict the impact of a target AHC based on physical statistic data for a defined set of physical statistics for the AHC impact model. In some implementations, an AHC impact model can be associated with a specific population or population cohort of users 120 selected by demographic information, geographic location, or other similar factors. The machine learning training module 230 can train multiple AHC impact models for the same target AHC, with each AHC impact model having a different combination for applicable population and physical statistics. For example, the machine learning training module 230 can construct an AHC impact model using a combination of RHR, step count, and sleep amount to predict the onset of an ILI. Using multiple categories of gathered wearable activity data in the same AHC impact model can provide better prediction of AHC onset, according to some embodiments. For example, a certain minority of users 120 in a given population can exhibit opposite to trend behavior in one or more physical statistics (for example, a minority of users may experience a drop in RHR after ILI onset as opposed to an increase in nRHR as can be expected based on an average user). In some implementations, the machine learning prediction system 110 uses AHC impact models combing physical statistic data in multiple categories to predict AHC onset not only to generally improve accuracy, but to account for situations where one or more categories of wearable activity may not align with expected trends for the AHC.

An AHC impact model can take recent physical statistic data for a user (for example, containing physical statistics from the current day and 3 previous days) and return a probability that a user 120 is experiencing the AHC for each of one or more days. An AHC impact model can provide a probability that the user has the AHC on the current day (or the most recent day physical statistic data is available for the user 120), on a specific future day (such as if the user 120 is likely to begin experiencing AHC symptoms tomorrow), or had the AHC on a previous day (such as if the (PSD indicates the user 120 began experiencing symptoms yesterday). In other embodiments, an AHC impact model can be trained to return a probability that the has or will imminently have the AHC, for example, based on the probability that the user has the AHC on one or more days. Similarly, AHC impact models can be trained to monitor recovery from an AHC, returning a probability a user 120 has recovered from the AHC and/or a probability the user 120 has not recovered from the AHC.

To train an AHC impact model, the machine learning training module 230 can assemble a training data set based on gathered physical statistic data and AHC event data from the illness reporting module 215. In some implementations, the machine learning training module 230 first assembles an initial training set of users 120 associated with the target AHC. A user can be selected for the training set if the user's stored physical statistic data is associated with an AHC event flag for the target AHC (for example, placed there based on the user's response to a survey from the illness reporting module 215). For example, when assembling a training data set for an ILI, the machine learning training module 230 can select users 120 who exhibited a fever or other ILI symptoms for which the machine learning prediction system 110 has RHR data (such as from a health sensor 125 of the user) for that user 120 during the same time range as the known ILI symptoms. In some implementations, the machine learning training module 230 adds additional, healthy users 120 into the training set. This initial training data set can be further refined, for example by removing users 120 who have experienced multiple instances of an AHC within a short time frame (for example, users 120 associated with instances of different AHCs within close proximity or users 120 who appeared to have the target AHC more than one time with a short gap in between), as the impact of any one instance of an AHC might not be clear for those users. Similarly, the initial training data set can be refined by removing users 120 with incomplete or low quality physical statistic data for the time range around the AHC event, for example, when the user 120 is missing data for one or more physical statistics the model (such as if the physical statistic data associated with a user contains no RHR data) will be based on or when significant gaps exist in all gathered physical statistic data for that user 120 during the time range to be analyzed.

In some embodiments, the training data set includes all available physical statistic data for users 120 in the training data set between preset dates (for example, the months of January and February of a given year) for which the data is available. In other implementations, analysis for each user 120 in the training data is based on physical statistic data for a time range around the known "day 0" onset of the target AHC. For example, the training data set can contain date from one week before the onset of the target AHC to one week after the AHC onset. The machine learning training module 230 can select the length and type of timeframe for analysis based on any suitable factors, including the availability of physical statistic data and the target AHC (for example, how long the target AHC is expected to last can affect the length of timeframe needed to model the impacts of the AHC).

AHC impact models can be based on normalized physical statistic values relative to a baseline (expressed as a percentage or absolute difference from a determined baseline for the user 120 in that physical statistic). In some implementations, the machine learning training module 230 can calculate per-user 120 normalized baselines of each collected physical statistic (for example, normalized RHR as described above, as well as a normalized step count and a normalized sleep amount for a user) for each user in the training data set. In some implementations, an individual baseline determined by the individual baseline module 220 is used as the baseline for the AHC impact model. In other embodiments, machine learning training module 230 can calculate a baseline for each physical statistic for the AHC impact model based on the physical statistic data in the days before the labeled onset of the AHC. For example, the baseline RHR for a user can include the mean and standard deviation of that user's RHR calculated for the recorded days before an ILI onset. In some embodiments, the training data can show an increase in normalized RHR compared to the baseline RHR which is correlated with ILI symptoms (such as fever) which can be captured by an ILI impact model.

In some implementations, the machine learning training module 230 generates simple rule-based models to determine AHC onset, for example, a model that detects an ILI onset based on a target day's (i.e. today's) average normalized RHR being higher than a certain, individual-specific, threshold.

In other embodiments, the machine learning training module 230 uses machine learning techniques to train AHC impact models that take into account multiple days of context and/or more than one physical statistics to predict if a user 120 has the AHC on a given day. For example, the machine learning training module 230 can use a gradient boosting techniques to generate a machine learning model (trained on the training set of user data comprising users with a known AHC and healthy users) to predict ILI onset with greater precision than the previously described rule-based models. For example, a machine learning model can be trained to predict current ILI onset using input features of nRHR from today and three previous days (i.e. four features, each containing the nRHR for one of four individual days including today). Similarly, machine learned AHC impact models can be trained using a combination of physical statistics as input features (such as a combination of nRHR, step count, and sleep time).

The machine learning training module 230 can use neural networks, deep learning techniques, gradient-boosting techniques, or another machine learning technique or combination of machine learning techniques to generate AHC impact models based on a training data set based on user physical statistic data from the physical statistic data module 210 and AHC events collected by the illness reporting model 215. For example, the machine learning training model can use machine learning techniques such as linear support vector machine (linear SVM), boosting for other algorithms (e.g., AdaBoost), neural networks, deep learning, logistic regression, naïve Bayes, memory-based learning, random forests, bagged trees, decision trees, boosted trees, or boosted stumps in various embodiments. In some implementations, the machine learning training module can re-train one or more AHC impact models for an AHC periodically or based on additional training data (physical statistic data and/or labeled AHC events) becoming available. AHC impact models can be stored in the model store 235 for later use by the prediction engine 250. For example, the machine learning training module 230 can train a machine learning model configured to predict the onset of an AHC (or the severity of an AHC) based on time series physical statistic data for a target user from a time period leading up to the (predicted) onset of the AHC.

In some implementations, AHC impact models trained by the machine learning training module 230 can have a ROC AUC (the Area Under the Curve of the Receiver Operating Characteristic curve) which is too low for the AHC impact models to serve as a standalone diagnostic test. AHC impact models can exhibit varying ROC AUC based on the machine learning techniques used and the amount, selection, and quality of physical statistic data used as inputs to the AHC impact model. An example AHC impact model using a combination of several physical statistics can exhibit a ROC AUC of between 0.6 and 0.7 and can therefore be used as an indication of the AHC (but not a diagnosis for the AHC) to trigger one or more interventions (including a follow up diagnostic test).

Acute Health Condition Burden Estimation

In some implementations, the burden calculation module 240 can measure the burden of an AHC on a population based on retrospective data about users 120 (for example, physical statistic data for the users 120). For example, the burden calculation module 240 can measure the burden of the flu (or another ILI) on a population based on physical statistic data for the users. By learning what patterns of flu look like, the burden calculation module 240 can, for instance, quantify that 10,000 steps/day are lost for people affected by the flu (as a population level average), or 30 minutes of additional sleep are needed during 2 or more days during the flu period, or the average RHR increases by 1 beat/minute for 3 days on average when a user is affected by the flu.

Measuring the burden of an AHC in the wild can provide public health benefits, for example, only a small percentage of flu events are reported to the health care system, leaving the majority of the burden of the flu on society unassessed. Further, even when cases of the flu are reported to the health care system, the burden in terms of lost productivity (sick days), sleep deprivation, and overall decrease in health status is unmeasured using traditional methods. Similar conditions exist for other AHCs for which the burden calculation module 240 can measure a population-level burden.

AHC burden measurement via physical statistic data can be accurate and fine grained, allowing for comparative effectiveness analyses of different treatments or strategies for dealing with the AHC. For example, the burden calculation module 240 can aid in evaluating flu treatments (e.g., antivirals) or vaccine impact in modulating the flu in real world settings. To perform a comparative effectiveness analysis, the burden calculation module 240 can utilize additional received data about treatments taken by each individual such as, medication taken and vaccine taken information for the set of users 120 (provided, for example, in surveys from the illness reporting module 215). For example, a comparative effectiveness analysis may find that one antiviral treatment is more/less effective than competitors in reducing lost physical activity, sleep deprivation, and overall quality of life due to flu impact. Similarly, a comparative effectiveness analysis can show that people who are vaccinated against the flu but end up getting the flu (as the flu vaccine has is not 100% effective at preventing the flu) get a flu that impairs their physical activity (steps), sleep, and RHR more mildly than unvaccinated users who get the flu.

As described above, in some embodiments, an individual baseline for user can be used to determine a residual from a user's normal activity during periods of self-reported AHC. In some implementations, the treatment effect of an AHC on physical statistic data is estimated as a deviation from the user's baseline predicted physical statistics. In embodiments with a strong (non-AHC) baseline, the burden calculation module 240 can subtract received physical statistic data indicating an AHC from the baseline, thus obtaining residuals which may represent the burden of flu on that individual user 120. Other embodiments of the machine learning prediction system 110 can use more sophisticated models for the residuals, in order to eliminate additional confounders either unobserved or only partially captured by the baseline model. Such residual models may include impulse priors or spline-based models that can capture the expected shape of the physical statistic data over time.

In some embodiments, the computed burden of an AHC corresponds to the Individual Treatment Effect (ITE) of the AHC on the behavior/physiology of an individual. Using calculated ITEs, the machine learning prediction system 110 can monitor how ITEs are evolving over time to detect patterns of AHC at the population level (surveillance) or provide individual-level symptom tracking and forecast to individual users 120. Similarly, the machine learning prediction system can compute Average Treatment Effects (ATEs) for users 120 in different population cohorts based on ITEs of the users within a cohort. In some embodiments, the users of a cohort are similar (for example, sharing similar demographics), and users within a cohort were exposed to different treatments (e.g., antiviral) or different preventive care measures (e.g., vaccine) for the AHC. The machine learning prediction system 110 can then estimate effectiveness of different treatments and perform comparative analyses across treatments/preventative care measures (which can later be prospectively validated). When parametric methods are used to estimate flu burden separately for these cohorts, the machine learning prediction system 110 can directly compare parameter estimates to measure differences in AHC burden, for example, in the peak or duration of the change in activity or RHR compared to baseline. In some embodiments, the machine learning prediction system uses non-parametric methods to compare the integral of the burden estimated for each cohort by taking the sum of the daily residuals (relative to predicted baseline activity) of these activity measures. Because some population cohorts have different rates of getting an AHC (for example, children and older adults have higher flu infection rates than adults 18-49 years old), causal inference techniques such as propensity score matching or use of the Augmented Inverse Probability Weighted Estimator can be used to estimate treatment ATEs for each cohort. In some implementations, the machine learning prediction system 110 gathers propensity estimates from health organizations or from flu survey data collected from users 120 of the machine learning prediction system 110.

Acute Health Condition Prediction

As described above, the machine learning prediction system 110 can use generated AHC impact models to predict AHC onset or monitor AHC recovery in an individual based on current physical statistic data for that individual. Using the predictions, the prediction engine 250 can recommend interventions based on predicted AHC onset (or an abnormal recovery) to address or mitigate the effect of the AHC on an affected individual user 120, group, or population. The prediction engine 250 of FIG. 2 includes an onset prediction module 260, recovery monitoring module 265, and an intervention module 270.

The onset prediction module 260, according to some implementations, can predict if a user has a specific AHC in a user 120 based on an AHC impact model for that AHC and physical statistic data for the user 120. The onset prediction module 260 can operate for AHCs that have a gradual onset, or where an affected individual may not realize they have the AHC for some time (even if their physical statistics are being affected by the AHC). For example, implementations of the onset prediction model 160 can be used to predict the onset of the flu, other ILIs (such as COVID-19), or infectious illnesses where an infected individual does not show full symptoms until sometime after contracting the AHC.

The onset prediction module 260 can use AHC impact models generated by the machine learning training module 230 predict AHC onset for users with no associated symptom data (in real time or in near-real time). To predict the onset of an AHC in a user 120, the onset prediction module 260 can retrieve an AHC impact model for the AHC (for example, from the model store 235), input recent physical statistic data for the user 120 (such as physical statistic data collected by the physical statistic data module 210), and calculate a resulting probability that the user 120 has the AHC (an "AHC probability") using the AHC impact model. In some implementations, the onset prediction module 260 sends an AHC prediction (including the AHC probability for the user 120 and, for example, details about the user 120) to the intervention module 270, which can determine if the machine learning prediction system 110 will trigger an intervention based on the prediction. The intervention module 270 and the selection of interventions will be discussed further below.

In some implementations, the onset prediction module 260 can predict AHC onset for a user 120 regularly (for example, on a daily or weekly basis), based on receiving physical statistic data for the user 120, based on an anomaly in recently received physical statistic data (for example, a RHR below a baseline RHR for the user), based on a user 120 report of a recent AHC event, in response to a request by the user 120 to check for AHC onset, or for another suitable reason. In some implementations, the frequency of automatic AHC onset predictions can be based on the specific AHC, seasonal or contextual factors, or demographic features of each user 120 (such as the age of the user 120 or a risk category of a user 120 for a specific AHC). For example, seasonal AHCs (such as the flu) can be checked more frequently during the associated seasons. Each distinct AHC monitored by the machine learning prediction system 110 can be checked by the onset prediction module 260 based on different conditions. In some implementations, users 120 can request the machine learning prediction system 110 to check for an AHC or set a preference setting affecting if and how often the machine learning prediction system 110 will check for AHC onset.

The recovery monitoring module 265 can monitor the recovery of users known to have (or have recently had) an AHC. For example, the user 120 can have scheduled surgery for which a recovery period is necessary, or the machine learning prediction system 110 receives a report that the user has an injury, illness, or other AHC (self-reported or through another source). In some implementations, the recovery monitoring module 265 uses *PDS data to determine if the user's recovery is still on track relative to a standard recovery modeled through an AHC impact model for the AHC. For example, if the effects of a surgical recovery for a certain procedure normally last a week, but if the recovery monitoring module still detects the effects after 10 days, the machine learning prediction system 110 can trigger an intervention.

Similar to the onset prediction module 260, the recovery monitoring module 265 can retrieve an AHC impact model for the AHC in question (for example, from the model store 235), input recent physical statistic data for the user 120 (such as physical statistic data collected by the physical statistic data module 210), and calculate a resulting AHC probability. AHC probabilities calculated by the recovery monitoring module 265 can represent the probability that the user 120 is experiencing complications or other delays in recovery in comparison with an expected recovery, according to some embodiments. The recovery monitoring module 265 can then send an AHC prediction including the AHC probability for the user 120 to the intervention module 270, which can determine if the machine learning prediction system 110 will trigger an intervention based on the prediction.

The intervention module 270 can recommend or automatically perform interventions based on AHC predictions made by the onset prediction module 260 and/or the recovery monitoring module 265. Interventions recommended by the intervention module 270 can notify the user of the potential AHC, mitigate the impact of the AHC on a population, treat the AHC, or provide for further diagnosis of the AHC, according to some embodiments. The interventions taken by the intervention module 270 can depend on the AHC, the user 120 (for example, based on user demographics, available information about the user 120, and/or preference settings of the user), and the AHC probability of the prediction.

In some embodiments, the intervention module 270 selects from a set of applicable interventions for each AHC prediction received from the onset prediction or recovery monitoring modules 260 and 265. Each AHC monitored by the machine learning prediction system 110 can be associated with a set of one or more possible interventions that can be initiated by the intervention module 270 in response to an AHC prediction for that AHC. A single AHC prediction can result in more than one intervention for the associated user 120. Interventions available to the intervention module 270 can be applicable across a set of different AHCs (such as sending a notification of the AHC prediction to the user 120) or specific to a single AHC (such as sending a specific diagnostic test designed to diagnose a specific AHC). Similarly, interventions can be based on if the AHC prediction was from the onset prediction module 260 or the recovery monitoring module 265 (for example, scheduling diagnostic appointment for an AHC instead of a follow up appointment for an AHC being recovered from).

In some implementations, each intervention is associated with an intervention threshold which the intervention module can use to determine if the intervention should be initiated for a given AHC prediction. For example, the intervention module 270 can compare the AHC probability of an AHC prediction to the intervention threshold for each possible intervention to determine which (if any) interventions should be initiated in response to the AHC prediction. More expensive, inconvenient, or limited (such as a doctor's appointment) can be assigned higher intervention thresholds than less costly interventions (such as a notification to the user), according to some embodiments. In addition, the intervention module 270 can select to initiate (or not initiate) an intervention based on additional factors (in combination with the AHC prediction), such as user 120 demographics or preference selections, or other selected interventions (for example, interventions may be mutually exclusive or counterproductive if performed together). In some implementations, the intervention module 270 uses intervention thresholds selected for relatively high precision to provide reasonably sure alerts. Use of an intervention threshold set for high precision may sacrifice recall (for example, only predicting ~10% of the true cases of an AHC), but an intervention that is triggered is more likely to be triggered based on an actual AHC event rather than a false positive.

Similarly, some interventions can be associated with relative intervention thresholds, where the AHC probability from an AHC predictions is ranked or otherwise compared with a set of other AHC predictions for that AHC made during the same day, week, or other defined time period to determine which AHC predictions of the set receive the intervention. For example, interventions can be selected based on a "top K" threshold where the K AHC predictions with the highest AHC probabilities receive the intervention or a "top %" threshold where a percentage of the AHC predictions with the highest AHC probability receive the intervention. Relative intervention thresholds can be useful for interventions which may have a limited supply due to logistical constraints, cost, or limited availability. In some implementations, relative intervention thresholds are used in combination with other intervention thresholds, such as an intervention selecting the top 150 AHC predictions with an AHC probability above 0.9 to receive the intervention.

As described above, the intervention module can initiate interventions that are carried out by (or partially by) an intervention system 150 separate from the user 120 and the machine learning prediction system 110. The intervention system associated with each initiated intervention can differ based on the selected intervention and the user 120 receiving the intervention. For example, if the intervention is to schedule a doctor's appointment, the intervention system 150 can be a specific doctor of the user 120.

AHC Applications

In some implementations, the set of interventions associated with an AHC can include one or more messages sent to the user 120 notifying the user of the AHC prediction and including instructions to mitigate the effects of the AHC, instruct the user how to prevent the AHC, and/or reduce the spread of the AHC depending on the properties of the AHC. For example, the intervention module 270 can send a message to a user 120 instructing the user to practice social distancing techniques or other spread-minimizing actions. If the AHC is the flu (or COVID-19 or another ILI) such a message might read "you look like you may be coming down with the flu, consider minimizing contact, here's a link to CDC guidelines." In cases of an infectious AHC (such as COVID-19 or an ILI), the intervention message can instruct the user 120 to test themselves and input the results to a contact tracing resource (such as a contact tracing application) and/or to check the contact tracing resource to see if they have been exposed to the AHC.

As described above, the intervention module 270 can also recommend or automatically schedule doctor appointments on predicting AHC onset. In some implementations, the intervention module 270 can interface with a doctor's office or other healthcare provider (as an intervention system 150) to schedule or recommend scheduling a doctor's appointment for the associated user 120. For example, some users 120 can be diagnosed with an AHC at a point of care (such as a hospital or doctor's office) but sent home for treatment due to low severity of current symptom manifestations. The machine learning prediction system 110 can be used to monitor those users 120 for more severe symptoms occurring. In some implementations, a specifically trained AHC impact model can output a "probability of symptoms worsening" for this use case. On detecting more severe symptoms, the intervention module 270 can inform the user and/or point of care and, in some implementations, schedule an appointment at the point of care.

Similarly, the machine learning prediction system 110 can also monitor users 120 receiving specific treatments for an AHC (including experimental treatments or treatments with a risk of adverse effects). On detecting a worsening of symptoms (or other adverse effects) the intervention module 270 can notify a healthcare provider administering the treatment (or other relevant entity) to follow up with the user 120 and determine if adverse effects are experienced (and if they are related to the treatment). For example, developing vaccines requires specific monitoring of drug safety and effectiveness for which the machine learning prediction system 110 can be used to identify adverse effects in users 120 receiving the vaccine.

In some embodiments, the machine learning prediction system 110 can be used to monitor for symptoms of an AHC and schedule a diagnostic test for the AHC at a healthcare provider and/or have an at-home test sent to the user 120. Using the machine learning prediction system 110 to select users 120 to receive tests can be effective, even if implemented over a long time period (in contrast to relying on daily symptom polling of users 120, which will experience reporting fatigue and a potentially a loss in effectiveness over time) and provide higher probability of finding cases of the AHC than randomly selecting users 120 to test. In cases where there is a limited supply of tests (not adequate to cover all users potentially experiencing the AHC), using the machine learning prediction system 110 to triage users 120 to be sent tests can magnify the impact of the available tests in finding cases of the AHC. This application of the machine learning prediction system 110 will be discussed further below.

The intervention module 270 can also pool AHC predictions collected for users 120 belonging to a population cohort or group of users to take actions on a group level. For example, a subset of users 120 can be associated with an employer, large event (such as a conference, festival, or the like), or other large gathering of users 120 based on approved association by the user 120 or the like. For an infectious AHC, the intervention module 270 can aggregate each AHC prediction for users 120 associated with the group to determine an approximate rate of infection (or estimated number of users infected with the AHC) within the group based, for example, on the AHC probability associated with AHC predictions of users 120 in the group. If the approximate rate of infection (of the group) reaches an intervention threshold, the intervention module can notify an authority of the group (such as an employer, event organizer, or local government) of the approximate rate of infection (while not notifying the group authority of any specific (AHC predictions of users 120) and/or recommend other actions such as canceling large events, implementing spread-minimization policies at an office building, or the like.

Similarly, users 120 can be grouped based on geographic area and estimated rate of infection/number of infected users 120 can be aggregated by the intervention module 270 based on geographic groups. In some implementations, the geographic groups can be separated based on county, municipality, neighborhood, or other similar geographic designation. Using these groups, the machine learning prediction system 110 can detect "hotspots" of an infections AHC such as COVID-19 or the flu and transmit this information to local health authorities, which can inform decisions on public health policy, or easing/implementing restrictions due to the AHC. In some implementations, using the machine learning prediction system 110 predictions based on current data provides a timing advantage over delayed signals such as "number of hospitalizations" (which can result in significant lag time before a patient becomes sick enough to require hospitalization) when making policy changes.

EXAMPLE AHC Application: Testing Triage

Figure 3:
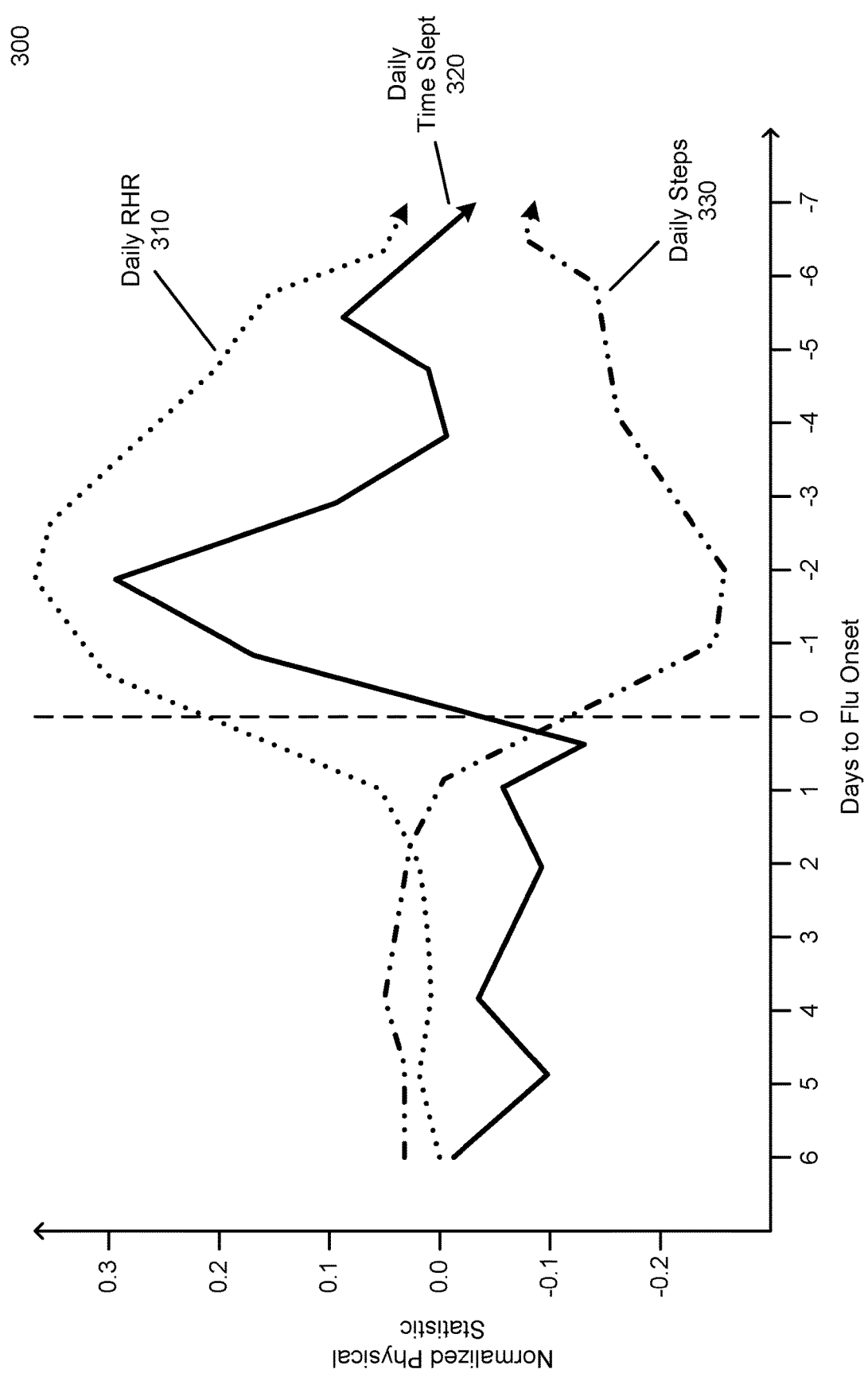
FIG. 3 is a graph illustrating example physical statistic trends for the flu, according to one embodiment.

FIG. 3 is a graph illustrating example physical statistic trends for the flu (or another ILI), according to one embodiment. The graph 300 of FIG. 3 shows the physical statistic data for normalized daily RHR 310, daily time slept 320, and daily steps 330 organized according to days until onset of the flu (when the user 120 would recognize flu symptoms). The graph 300 shows example trends in physical statistics for users 120 experiencing the flu (an AHC) that can be determined by the machine learning prediction system 110 based on user 120 *PDS data and reported AHC events (such as flu symptom reports) gathered by the illness reporting module 215. Trends detected for other AHCs (or even other ILIs) can exhibit different trends. Similarly, physical statistics other than RHR 310, time slept 320, and daily steps 330 can also exhibit trends for the flu, other ILIs, or other AHCs.

The graph 300 shows trend lines for daily RHR 310, daily time slept 320, and daily steps 330 from 6 days before flu onset to 7 days after flu onset. In this example, the daily RHR trend 310 and daily time slept trend 320 show increases in normalized RHR and time slept starting prior to flu onset. Similarly, the daily steps trend 330 shows a decrease in the day prior to flu onset. Therefore, daily RHR, time slept, and steps can be used as physical statistics for predicting onset of the flu or another ILI, according to some embodiments. Appendix A, a paper titled "Measuring COVID-19 and Influenza in the Real World via Person-Generated Health Data" discloses further details about physical statistic trends for COVID-19 compared to non-COVID-19 flu or other ILIs and is hereby incorporated by reference. For example, COVID-19 may cause a measurable increase in RHR (compared to a baseline RHR) in the days surrounding AHC onset.

In some situations (such as an outbreak of an infectious ILI like COVID-19), large amounts of tests on users 120 of a population can be performed to mitigate the spread of the outbreak, for example to recognize and contain infected clusters. For example, "testing at home" technology can be used to mail test kits to user 120 to take a diagnostic test for the ILI in addition to "point of care testing" performed at a healthcare facility or other specific site. However, the testing capacity available to the general population can be limited (due to logistics or availability concerns). Additionally, testing the general population can rely on members of the general population to request a test on their own initiative, which can result in some users 120 meeting guidelines for a test waiting to request a test (or just not requesting a test). Therefore, the users 120 can be aided in the process of symptom recognition and following through by technology. In some cases, users 120 can be polled daily to report their symptoms and the machine learning prediction system 110 can have tests shipped to those who report a constellation of symptoms consistent with the *ILI (such as COVID19 infection). However, over an extended period of daily polling users 120 may experience reporting fatigue and a corresponding drop in compliance/accuracy of the polling. Similarly, randomly assigning tests can result in tests on users 120 unlikely to be infected with the ILI. Therefore, the machine learning prediction system 110 can implement a "testing triage" system using a trained AHC impact model for the ILI to help determine which users 120 to be sent tests. In some implementations, as compared to randomly sampling a set of users 120 to poll every day for symptoms, the machine learning prediction system 110 system can be significantly more efficient in finding individuals that will test positive for the ILI.

As described above, the machine learning prediction system 110 can gather physical statistic data of users through the physical statistic data module 210 and augment that gathered data with symptom reports gathered by the illness reporting module 215. Using gathered training data, the machine learning module 230 can determine an AHC impact model for the ILI. Table 1 shows statistics of three AHC impact models designed to predict ILI onset based on different amounts of physical statistic data input data.

TABLE 1

|  | Input Data | AUROC | Precision | Approximate Gain |
|---|---|---|---|---|
| Forecasting model | Days −7 to −1 | .65 | .0471 | 1.5x |
| Nowcasting model | Days −7 to 0 | .67 | .0644 | 2x |
| Detection model | Days −7 to 3 | .69 | .0979 | 3x |

Table 1 includes statistics for a "forecasting model," a "nowcasting model," and a "detection model," with needed input data, AUROC, precision, and an approximate gain relative to random testing for each. In some implementations, testing can be assigned to users 120 based on a "top K" intervention threshold (as describe above) to select a certain number of users the model is most confident are experiencing the ILI to receive the test. The approximate gain is calculated based on a ratio of precision of the model over prevalence of the ILI in the sample set. The approximate gain can measure an advantage of the model over a randomized testing strategy in finding users 120 infected with the ILI.

The forecasting model shown in table 1 takes input for the 7 days prior to the target day (for example, if using current data, the forecasting model would predict an ILI onset tomorrow). Out of the three example models, the forecasting model is the least accurate, but provides the most advance notice in onset prediction (and still provides a 1.5× gain, depending on the chosen top K threshold). The nowcasting model takes input for the 7 days prior to the target day and the target day itself (for example, if using current data, the forecasting model would predict an ILI onset today). Finally, the detection model uses data for the 7 days prior to the target day, the target day itself, and three days after the target day (for example, if using current data, the forecasting model would predict an ILI onset three days ago). The example detection model shows the best AUROC, precision, and gain, but requires data after the target day prediction.

Implementations of a testing triage system can select an AHC impact model (or a combination of models) based on the properties of the ILI, the test for the ILI, or the testing capacity of the system. For example, if testing capacity is severely limited a model that produces a higher gain might be chosen, but if quick identification of potential cases is the main concern a forecasting model can be chosen.

Machine Learning Prediction System Processes

Figure 4:
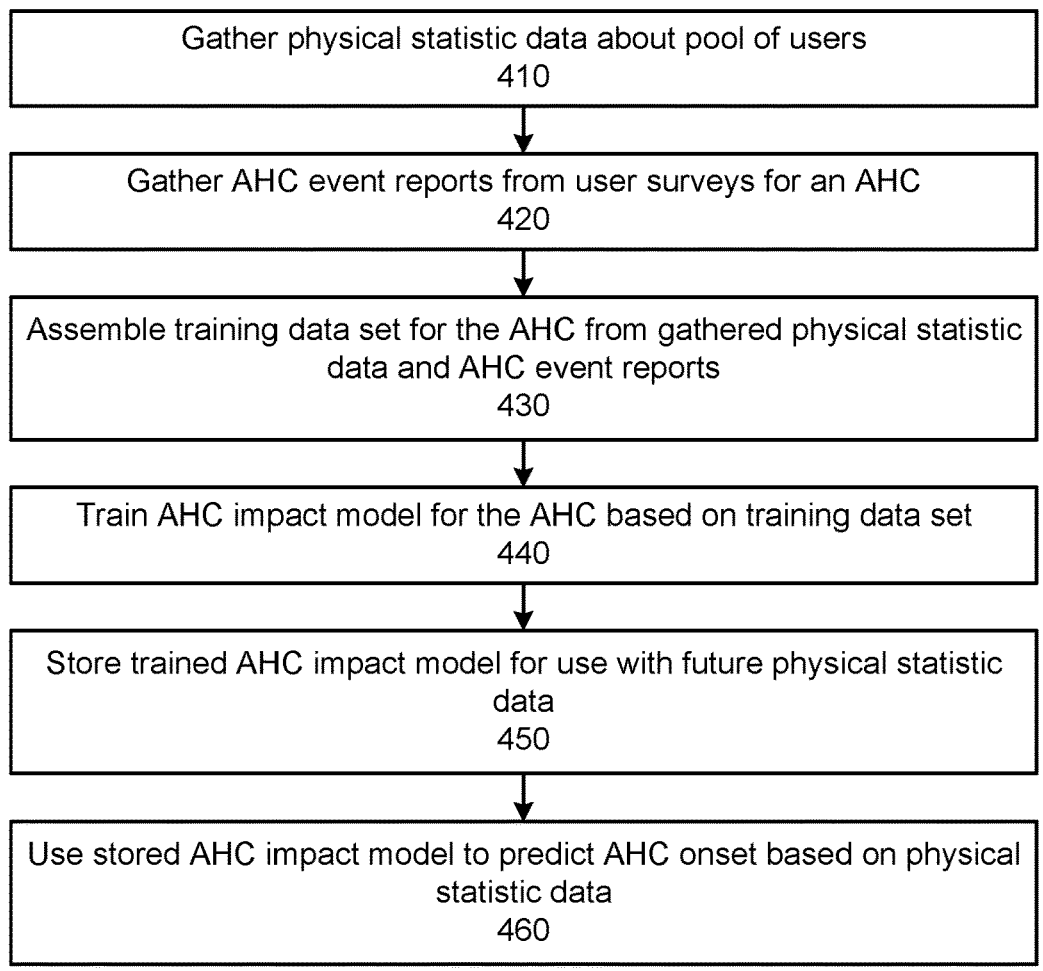
FIG. 4 is a flowchart illustrating an example process for generating a model of an acute health condition at a machine learning prediction system, according to an embodiment.

FIG. 4 is a flowchart illustrating an example process for generating a model of an acute health condition at a machine learning prediction system, according to an embodiment. The process 400 of FIG. 4 begins when a machine learning prediction system gathers 410 physical statistic data about a pool of users. For example, as described above, the machine learning prediction system can gather information from one or more health sensors of users of the machine learning prediction system. Then, the machine learning prediction system can gather 420 AHC event reports describing symptoms and/or confirmed cases of the AHC among the pool of users. For example, the gathered from user surveys as described above. Next, the machine learning prediction system can assemble 430 a training data set for the AHC using the gathered physical statistic data and AHC event reports and train 440 an AHC impact model for the AHC based on the assembled training data set. The trained AHC impact model can then be stored 450 and used 460 for prediction of AHC onset in users based on current physical statistic data. Similarly, an AHC impact model can be used to estimate the burden of the AHC on a population.

Figure 5:
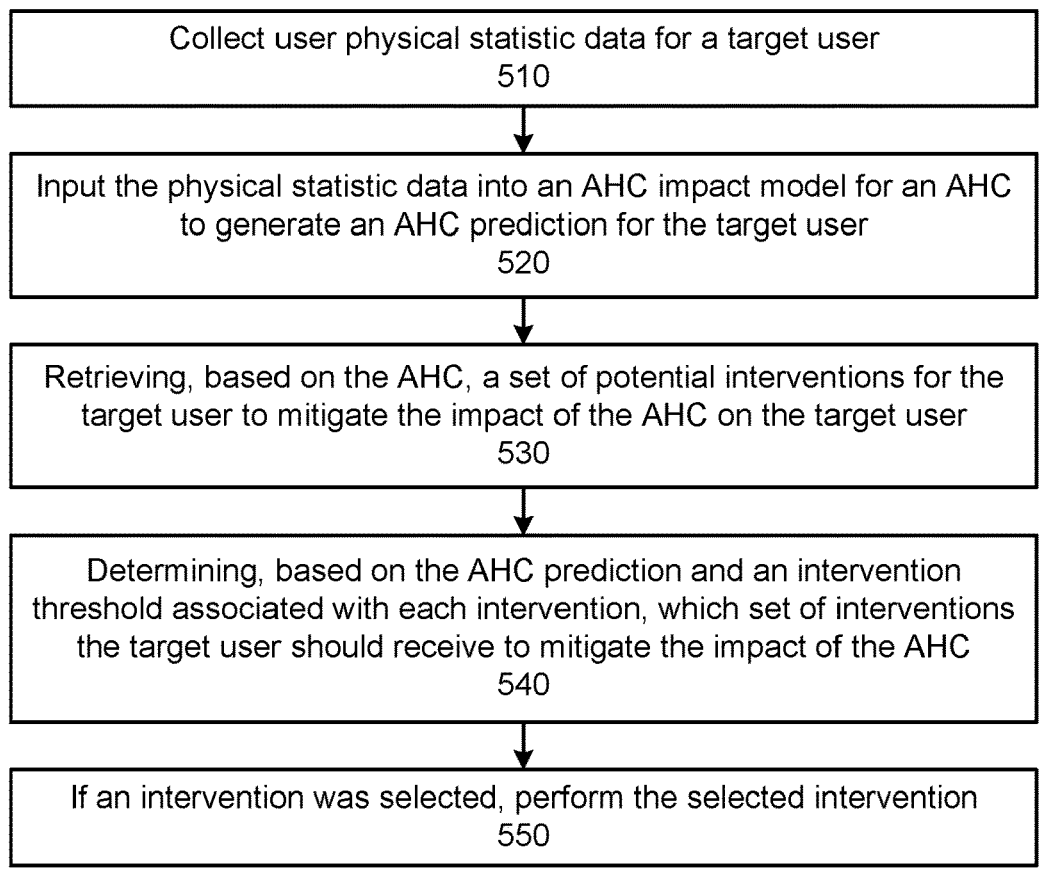
FIG. 5 is a flowchart illustrating an example process for providing an intervention to an individual user based on predicted onset of an acute health condition for the individual user based on a model of an acute health condition, according to an embodiment.

FIG. 5 is a flowchart illustrating an example process for providing an intervention to an individual user based on predicted onset of an acute health condition for the individual user based on a model of an acute health condition, according to an embodiment. The process 500 of FIG. 5 begins when a machine learning prediction system collects 510 user physical statistic data for a target user and inputs 520 the physical statistic data into an AHC impact model for an AHC. As described above, an AHC impact model can generate an AHC prediction for the target user including a confidence level or probability that the target user currently has the AHC and/or will soon experience the onset of symptoms of the AHC based on the target user's physical statistic data. Then, the machine learning prediction system can then retrieve 530 a set of potential interventions for the AHC which if implemented by the machine learning prediction system and/or the target user could mitigate the impact of the AHC on the user (or the population in the case of social distancing or other similar spread-limiting interventions). Out of the set of the interventions the machine learning prediction system determines 540 which interventions the target user should receive based on an intervention threshold associated with each intervention and the AHC prediction generated by the AHC impact model. If an intervention was selected, the machine learning prediction system can perform 550 the selected interventions, in some cases with the help of a third-party intervention system, as described above.

Figure 6:
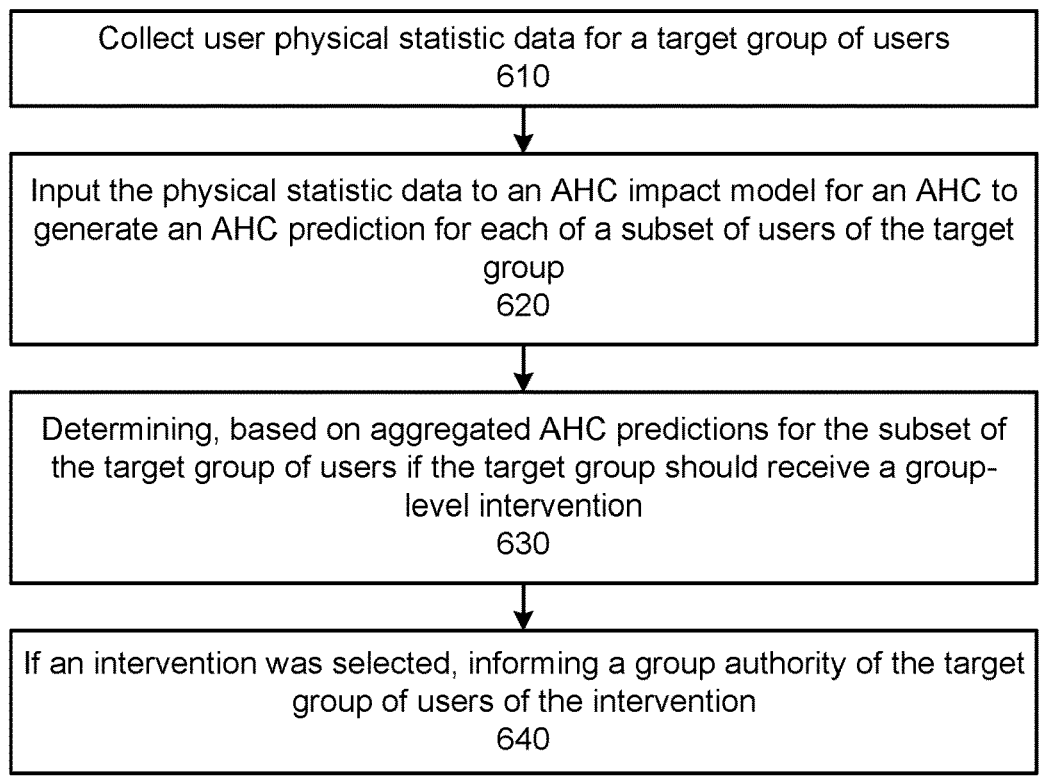
FIG. 6 is a flowchart illustrating an example process for determining a group level intervention for a target group using a model of an acute health condition to predict AHC onset for individual users of the target group, according to an embodiment.

FIG. 6 is a flowchart illustrating an example process for determining a group level intervention for a target group using a model of an acute health condition to predict AHC onset for individual users of the target group, according to an embodiment. The process 600 of FIG. 6 begins when a machine learning prediction system collects 610 user physical statistic data for users of a target group of users. Then, the machine learning prediction system inputs 620 gathered physical statistic data of a subset of users of the target group into an AHC impact model for an AHC. As described above, an AHC impact model can generate an AHC prediction for an individual user, for example including a confidence level or probability that the target user currently has the AHC and/or will soon experience the onset of symptoms of the AHC based on the target user's physical statistic data. Using the set of individual AHC predictions for each user of the subset of users, the machine learning prediction system can determine 630 if the target group should receive a group-level intervention (such as cancellation of an event or a policy change). The machine learning prediction system can then inform 640 a group authority of the target group of one or more recommended group-level interventions.

CONCLUSION

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method for selecting an intervention for an infectious disease, comprising:
   (a) training a machine learning model using a set of training data from a first population cohort comprising a plurality of users, the set of training data comprising a confirmed case of the infectious disease of a first user of the plurality of users and wearable sensor data from the plurality of users, wearable sensor data from a first user of the plurality of users comprising physical statistics and symptoms collected over a plurality of consecutive time periods and associated with the infectious disease, wherein at least one of the consecutive time periods is prior to an onset of the infectious disease and at least one of the consecutive time periods is after the onset of the infectious disease, wherein the first user is placed in the first population cohort based at least in part on a pattern of the wearable sensor data from the first user;
   (b) receiving, from a target user, physical statistics data for the target user, wherein the first population cohort comprises the target user;
   (c) predicting a probability of onset of the infectious disease for the target user within a subsequent interval of time by applying the trained machine learning model to the received physical statistics data for the target user;
   (d) placing the predicted probability into a group of predictions from a second population cohort comprising the target user, wherein a prediction of the group of predictions for a second user from the second population cohort is determined by performing steps (a)-(c) on the second user, wherein the second user is placed into the second population cohort based at least in part on a proximity of the second user to a plurality of additional users within the second population cohort;
   (e) automatically selecting the intervention based at least in part on the group of predictions from the population cohort; and
   (f) notifying the target user of the selected intervention based on the predicted probability.

2. The method of claim 1, wherein the intervention comprises modifying an interface displayed by a user device of the target user to display a notification with information warning the target user of the infectious disease.

3. The method of claim 1, wherein the intervention comprises automatically sending a test kit corresponding to the infectious disease to the target user.

4. The method of claim 1, wherein the intervention comprises automatically scheduling a doctor's appointment with the target user without input from the target user.

5. The method of claim 1, wherein the intervention is associated with a corresponding probability threshold.

6. The method of claim 1, wherein receiving the physical statistics data for the target user comprises receiving time series measurements of a set of physical statistics from a wearable health sensor of the target user.

7. The method of claim 1, wherein the set of training data further comprises infectious disease symptom data for the plurality of users.

8. The method of claim 7, further comprising sending, to the plurality of users, a survey requesting infectious disease symptom data.

9. The method of claim 1, wherein the infectious disease is an influenza-like illness.

10. The method of claim 1, wherein the infectious disease is COVID-19.

11. The method of claim 1, wherein the physical statistics data comprises a measurement of a physical statistic selected from the group of resting heart rate, activity level, daily step count, and sleep time.

12. The method of claim 1, wherein the physical statistics data comprises a measurement of a physical statistic selected from the group of respiration rate, heart rate variability, and galvanic skin response.

13. A non-transitory computer-readable storage medium comprising instructions which, when executed by a processor, cause the processor to perform the steps of:
   (a) training a machine learning model using a set of training data from a first population cohort comprising a plurality of users, the set of training data comprising a confirmed case of the infectious disease of a user of the plurality of users and wearable sensor data from the plurality of users, wearable sensor data from a first user of the plurality of users comprising physical statistics and symptoms collected over a plurality of consecutive time periods and associated with the infectious disease, wherein at least one of the consecutive time periods is prior to the onset of the infectious disease and at least one of the consecutive time periods is after an onset of the infectious disease, wherein the first user is placed in the first population cohort based at least in part on a pattern of the wearable sensor data of the first user;
   (b) receiving, from a target user, physical statistics data for the target user, wherein the first population cohort comprises the target user;
   (c) predicting a probability of onset of the infectious disease for the user within a subsequent interval of time by applying the trained machine learning model to the physical statistics data for the target user;
   (d) placing the predicted probability into a group of predictions from a second population cohort comprising the target user, wherein a prediction of the group of predictions for a second user from the second population cohort is determined by performing steps (a)-(c) on the second user, wherein the second user is placed into the second population cohort based at least in part on a proximity of the second user to a plurality of additional users within the population cohort;

(e) automatically selecting the intervention based at least in part on the group of predictions from the population cohort; and (f) notifying the target user of the selected intervention based on the predicted probability.

14. The non-transitory computer-readable storage medium of claim 13, wherein the intervention comprises modifying an interface displayed by a user device of the target user to display a notification with information warning the target user of the infectious disease.

15. The non-transitory computer-readable storage medium of claim 13, wherein the intervention comprises automatically sending a test kit corresponding to the infectious disease to the target user.

16. The non-transitory computer-readable storage medium of claim 13, wherein the intervention comprises automatically scheduling a doctor's appointment with the target user without input from the target user.

17. The non-transitory computer-readable storage medium of claim 13, wherein receiving the physical statistics data for the target user comprises receiving time series measurements of a set of physical statistics from a wearable health sensor of the target user.

18. The non-transitory computer-readable storage medium of claim 13, wherein the infectious disease is an influenza-like illness.

19. The non-transitory computer-readable storage medium of claim 13, wherein the physical statistics data comprises a measurement of a physical statistic selected from the group of resting heart rate, activity level, daily step count, and sleep time.

20. The non-transitory computer-readable storage medium of claim 13, wherein the physical statistics data comprises a measurement of a physical statistic selected from the group of respiration rate, heart rate variability, and galvanic skin response.

21. A method for training a machine learning system to predict onset of an infectious disease, comprising:

collecting first wearable sensor data from a population cohort comprising a plurality of users and at least a confirmed case of the infectious disease of a user of the plurality of users, the first wearable sensor data comprising physical statistics and symptoms collected over a plurality of consecutive time periods and associated with the infectious disease, wherein at least one of the consecutive time periods is prior to an onset of the infectious disease and at least one of the consecutive time periods is after the onset of the infectious disease, wherein the user is placed in the population cohort based at least in part on a pattern of the first wearable sensor data;

applying normalization to the first wearable sensor data to generate first normalized wearable sensor data;

creating a first training set comprising at least the first normalized wearable sensor data from the population cohort and the confirmed case of the infectious disease;

training a machine learning model of the machine learning system in a first stage using the first training set;

creating a second training set comprising the first training set and second wearable sensor data from the population cohort; and training the machine learning model of the machine learning system in a second stage using the second training set.

* * * * *

UNITED STATES PATENT AND TRADEMARK OFFICE
CERTIFICATE OF CORRECTION

Page 1 of 1

PATENT NO. : 12,033,761 B2
APPLICATION NO. : 16/926510
DATED : July 9, 2024
INVENTOR(S) : Luca Foschini, Eamon Caddigan and Raghunandan Melkote Kainkaryam It is certified that error appears in the above-identified patent and that said Letters Patent is hereby corrected as shown below:

In the Claims

Column 21, Line 35, Claim 1, "wearable sensor data from a first" should read --wearable sensor data from the first--

Column 21, Line 41, Claim 1, "at least one of the consecutive time periods" should read --at least another one of the consecutive time periods--

Column 21, Line 49, Claim 1, "predicting a probability of onset" should read --predicting a probability of the onset--

Column 22, Line 42, Claim 13, "infectious disease of a user" should read --infectious disease of a first user--

Column 22, Line 44, Claim 13, "wearable sensor data from a first user" should read --wearable sensor data from the first user--

Column 22, Line 49, Claim 13, "prior to the onset of the infectious disease" should read --prior to an onset of the infectious disease--

Column 22, Lines 49-50, Claim 13, "at least one of the consecutive time periods" should read --at least another one of the consecutive time periods--

Column 22, Lines 50-51, Claim 13, "after an onset of the infectious disease" should read --after the onset of the infectious disease--

Column 22, Line 57, Claim 13, "predicting a probability of onset" should read --predicting a probability of the onset--

Column 22, Line 58, Claim 13, "disease for the user" should read --disease for the target user--

Signed and Sealed this
Twentieth Day of August, 2024

Katherine Kelly Vidal
*Director of the United States Patent and Trademark Office*